(12) United States Patent
Khan et al.

(10) Patent No.: US 11,748,354 B2
(45) Date of Patent: Sep. 5, 2023

(54) DATA SHAPE CONFIDENCE

(71) Applicant: International Business Machines Corporation, Armonk, NY (US)

(72) Inventors: Shakil Manzoor Khan, Highland Mills, NY (US); Paul R. Bastide, Ashland, MA (US); Senthil Bakthavachalam, Yorktown Heights, NY (US)

(73) Assignee: International Business Machines Corporation, Armonk, NY (US)

( * ) Notice: Subject to any disclaimer, the term of this patent is extended or adjusted under 35 U.S.C. 154(b) by 208 days.

(21) Appl. No.: 17/033,845

(22) Filed: Sep. 27, 2020

(65) Prior Publication Data

US 2022/0100750 A1    Mar. 31, 2022

(51) Int. Cl.
*G06F 16/2455* (2019.01)
*G16H 10/60* (2018.01)

(52) U.S. Cl.
CPC ......... *G06F 16/2455* (2019.01); *G16H 10/60* (2018.01)

(58) Field of Classification Search
CPC .............................. G06F 16/2455; G16H 10/60
USPC ........................................................ 707/769
See application file for complete search history.

(56) References Cited

U.S. PATENT DOCUMENTS

| | | | |
|---|---|---|---|
| 6,466,936 B1 | 10/2002 | Ronström | |
| 7,292,956 B1 | 11/2007 | Guday et al. | |
| 8,566,121 B2 | 10/2013 | Ramasubramanian et al. | |
| 8,606,804 B2 * | 12/2013 | Merz ..................... | G06F 16/245 707/779 |
| 9,679,113 B2 | 6/2017 | Hanina et al. | |
| 10,320,569 B1 | 6/2019 | Wentz et al. | |
| 10,489,865 B1 * | 11/2019 | Dillard ................... | G06Q 40/12 |
| 11,113,294 B1 * | 9/2021 | Bourbie ............ | G06F 16/24568 |
| 11,158,412 B1 * | 10/2021 | Carlson .................. | G06F 18/214 |
| 11,304,699 B2 * | 4/2022 | Shelton, IV ..... | G06K 19/07749 |
| 2007/0118036 A1 * | 5/2007 | Hersh ..................... | A61B 5/022 600/490 |
| 2012/0141002 A1 * | 6/2012 | Urbano ................. | G01S 7/5205 382/131 |
| 2013/0064432 A1 * | 3/2013 | Banhazi ................. | A01K 29/00 382/110 |
| 2013/0138688 A1 * | 5/2013 | Anderson ......... | G06F 16/24544 707/769 |
| 2014/0364972 A1 * | 12/2014 | Minvielle .......... | G01N 33/0001 700/90 |
| 2015/0124264 A1 * | 5/2015 | Ramachandran .... | A61B 5/1079 356/601 |
| 2015/0369918 A1 * | 12/2015 | Tacke .................... | G01S 7/4863 702/150 |

(Continued)

OTHER PUBLICATIONS

Declercq, "Medication Adherence: Definitions, Calculations, and Statistical Modeling Strategies," Thesis, Vanderbiltm University, Aug. 10, 2018, 82 pages.

(Continued)

*Primary Examiner* — Hanh B Thai
(74) *Attorney, Agent, or Firm* — Peter J. Edwards

(57) ABSTRACT

A system determines a shape of incoming data, and determines, based on the shape, whether the data should be passed on to support answering a query. If the shape of the data suggests that the data is insufficient or may even be misleading, the system can gate the data or prompt for more.

20 Claims, 5 Drawing Sheets

(56) References Cited

U.S. PATENT DOCUMENTS

| | | | | |
|---|---|---|---|---|
| 2016/0371435 | A1* | 12/2016 | Pauletto | G06F 16/24573 |
| 2017/0091388 | A1* | 3/2017 | Zolla | G06F 16/254 |
| 2018/0052897 | A1* | 2/2018 | Namarvar | G06Q 10/0637 |
| 2018/0276672 | A1* | 9/2018 | Breed | G06Q 20/321 |
| 2019/0206563 | A1* | 7/2019 | Shelton, IV | A61B 1/051 |
| 2020/0117934 | A1* | 4/2020 | Mills, Jr. | G06T 7/60 |
| 2020/0203012 | A1* | 6/2020 | Kamath | A61B 5/002 |
| 2020/0294642 | A1* | 9/2020 | Bostic | G16H 50/20 |
| 2021/0090694 | A1* | 3/2021 | Colley | G16B 40/00 |
| 2021/0242899 | A1* | 8/2021 | Macleod | G01S 19/243 |
| 2021/0282624 | A1* | 9/2021 | Nichols | A61B 1/00059 |
| 2022/0092326 | A1* | 3/2022 | Mills, Jr. | G06T 3/4023 |
| 2022/0386946 | A1* | 12/2022 | Hilmisson | A61B 5/4812 |

OTHER PUBLICATIONS

Leslie et al., "Calculating Medication Compliance, Adherence and Persistence in Administrative Pharmacy Claims Databases," Research Gate, Aug. 2008, 9 pages, DOI: 10.1179/175709208X334614.

Greene et al., "A Novel Statistical Method for Assessing Effective Adherence to Medication and Calculating Optimal Drug Dosages," PLOS ONE, Research Article, Apr. 20, 2018, 17 pages, https://doi.org/10.1371/journal.pone.0195663.

"IoT System and Method for Assisting ELD (Electronic Log Devices) and HOS (Hours of Service)," ip.com, An ip.com Prior Art Database Technical Disclosure, ip.com No. IPCOM000260088D, ip.com Electronic Publication Date: Oct. 21, 2019, 5 pages.

"Aggregation of Plural Security Standards for Dynamic Remediation," ip.com, An ip.com Prior Art Database Technical Disclosure, ip.com No. IPCOM000257888D, ip.com Electronic Publication Date: Mar. 20, 2019, 3 pages.

"Method and System for Estimating Accuracy of Self-Reported Health Data," ip.com, An ip.com Prior Art Database Technical Disclosure, ip.com No. IPCOM000234565D, ip.com Electronic Publication Date: Jan. 17, 2014, 3 pages.

"Health Check Process for a Storage Area Network (SAN) Volume Controller (SVC)," ip.com, An ip.com Prior Art Database Technical Disclosure, ip.com No. IPCOM000214104D, ip.com Electronic Publication Date: Jan. 10, 2012, 7 pages.

* cited by examiner

DATA SHAPE CONFIDENCE

BACKGROUND

An entity (such as a company) seeking to perform data analysis will often submit a "query" to a data source (such as a server or device). The data source replies to the query with data, which the entity may use to perform its analysis.

For example, in the healthcare field, a company may seek to determine a patient's adherence to a medication plan (e.g., whether/how reliably the patient has been administered a designated medication according to a plan's schedule). Some medication devices are now capable of recording data regarding use. For example, an inhaler may be equipped to record when it was used, how much medication a user received, and the like. This data can be synced to a user's mobile device.

SUMMARY

Some embodiments of the present disclosure can be illustrated as a method. The method comprises receiving a query from a query source. The method further comprises receiving a dataset. The method further comprises acquiring an expected data shape. The method further comprises determining a data shape of the dataset. The method further comprises comparing the data shape to the expected data shape. The method further comprises determining, a confidence factor based on the comparison of the data shape to the expected data shape. The method further comprises detecting that the confidence factor is above a confidence threshold. The method further comprises transmitting (in response to the detecting) a reply to the query source in response to the query, the reply based on the dataset.

Some embodiments of the present disclosure can also be illustrated as a computer program product comprising a computer readable storage medium having program instructions embodied therewith, the program instructions executable by a computer to cause the computer to perform the method discussed above.

Some embodiments of the present disclosure can be illustrated as a system. The system may comprise memory and a central processing unit (CPU). The CPU may be configured to execute instructions to perform the method discussed above.

The above summary is not intended to describe each illustrated embodiment or every implementation of the present disclosure.

BRIEF DESCRIPTION OF THE DRAWINGS

The drawings included in the present application are incorporated into, and form part of, the specification. They illustrate embodiments of the present disclosure and, along with the description, serve to explain the principles of the disclosure. The drawings are only illustrative of certain embodiments and do not limit the disclosure. Features and advantages of various embodiments of the claimed subject matter will become apparent as the following Detailed Description proceeds, and upon reference to the drawings, in which like numerals indicate like parts, and in which:

Figure 1:
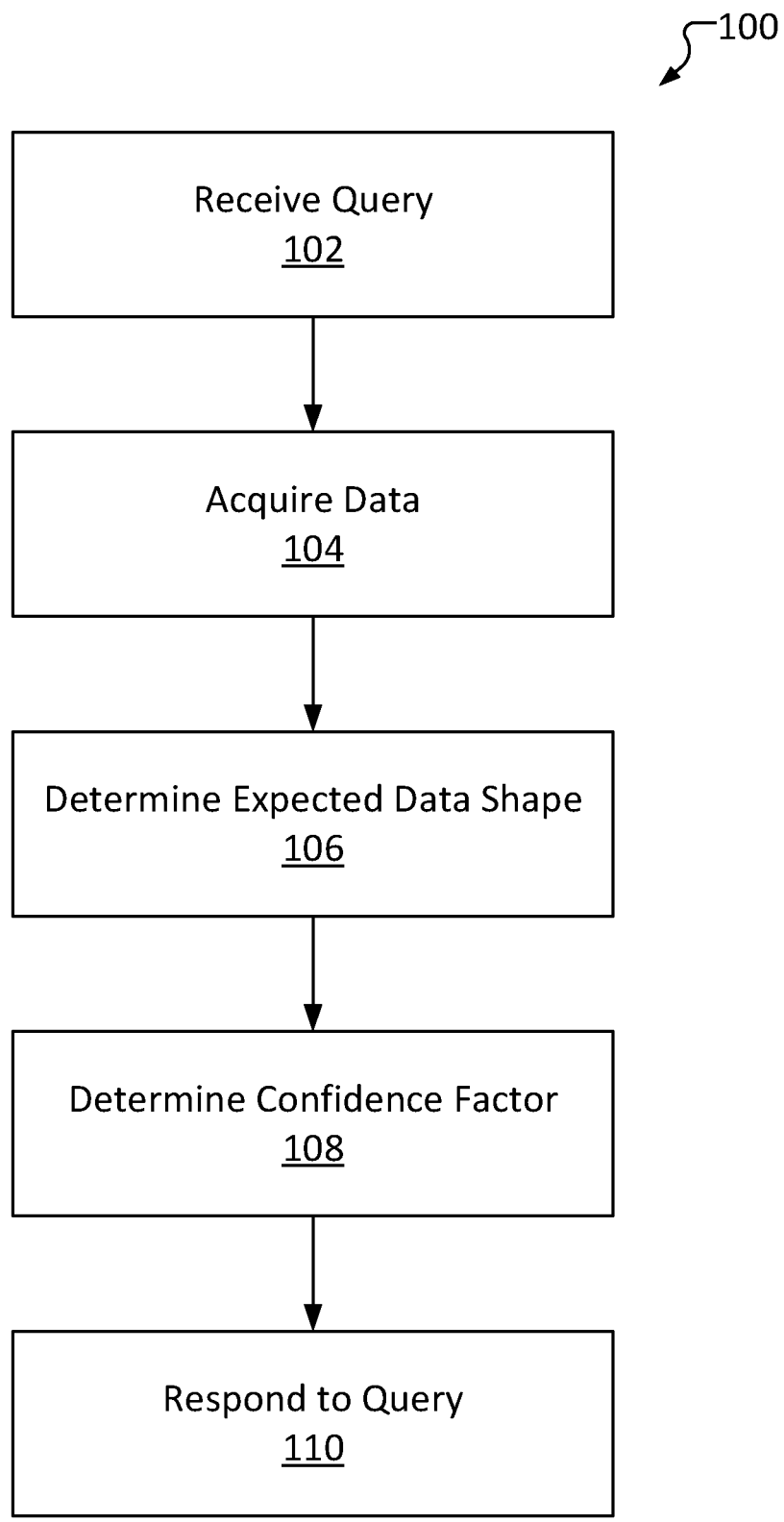
FIG. 1 is a high-level query response method based on data shape, consistent with several embodiments of the present disclosure.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention.

DETAILED DESCRIPTION

Aspects of the present disclosure relate to systems and methods to determine data shape confidence. More particular aspects relate to a system to receive data, determine a shape of the data, determine a required data shape in view of a query, and determine a confidence rating of the received data.

Throughout this disclosure, reference is made to one or more "queries." As used herein, a "query" may refer to a request for information. Queries may be received from external sources via, for example, a network. For example, in some embodiments an adherence query may be received, requesting data on a patient's adherence to a medication plan.

Systems and methods consistent with the present disclosure may receive a dataset from any number of sources and determine a response to the query based on the received dataset(s). In order to determine the reply, an example system may determine an expected data shape based on the query, the received dataset, an industry standard, a combination thereof, etc.

Figure 4:
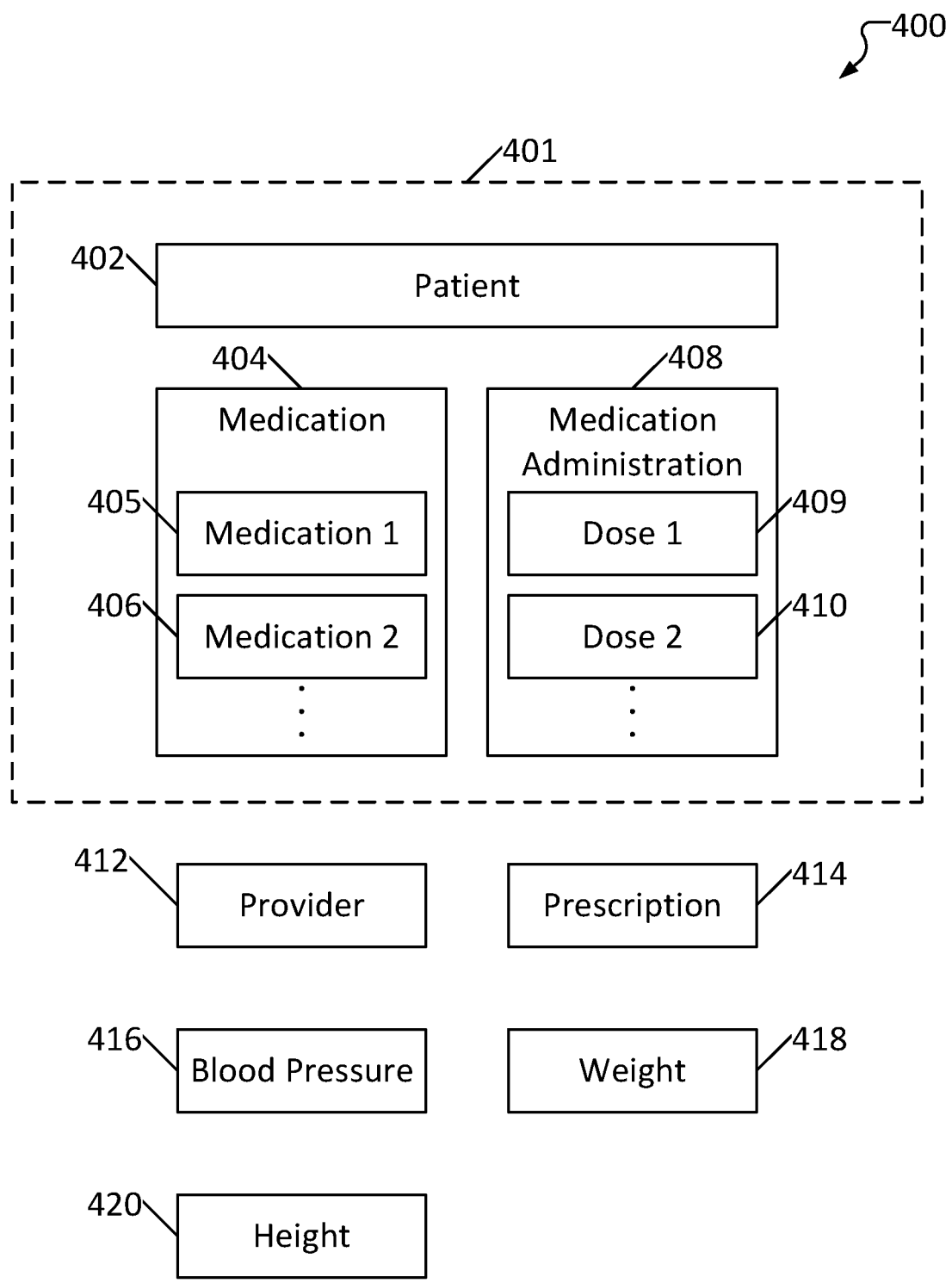
FIG. 4 is a block diagram illustrating an example expected data shape consistent with several embodiments of the present disclosure.

As used herein, a dataset's "shape" refers to values of the dataset as well as metadata such as, for example, which types of data ("data fields") the data describes, a number of columns and/or a number rows of the data, a completeness of the data, a number of supporting references, or the like. Put differently, a data shape describes several attributes of a dataset, such as data fields (e.g., "patient name," "medication name," "time of administration of medication," etc.), values contained within the data fields (e.g., "John Doe," "Acetaminophen," "10:26 A.M.," etc.), size of the dataset, etc. An example dataset is depicted in FIG. 4. Values in a received dataset are categorized by data field.

In responding to a query, multiple sources of data may provide data in a variety of states, using a variety of different methods. Data sources can include, for example, an application executing on a user's mobile device, an external database, etc. For example, a first external data source may provide a first dataset upon connecting to the internet (e.g., an application executing on a user's mobile device may attempt to sync daily, but may be unable to sync for an extended duration if it is disconnected; upon reconnecting, the application may transmit a dataset including all previously-unsent data). Further, the first data source may only provide data on a limited number of data fields. Meanwhile, a second data source may provide a second source dataset periodically, with the second source dataset including data on different data fields. Overlap is also possible; a third data source may provide its own datasets periodically as well, with the third source's datasets including some data fields covered by the first source's datasets and some data fields covered by the second source's datasets, etc.

The shape of received dataset(s) can be compared to an expected data shape to determine whether the dataset(s) will assist or be otherwise useful in responding to the query. In other words, comparing an expected data shape used for a complete reply to a hypothetical query to a shape of a received dataset enables a system to determine whether the received dataset would make a relevant reply to the query. For example, if a query is requesting a number of items sold in a store, a received dataset describing overhead for the store (payroll, rent/mortgage, utility bills, etc.) would have a different data shape than the expected shape of a reply, enabling a system to determine that the received dataset is not a useful reply to the query.

FIG. 1 is a high-level query response method 100 based on data shape, consistent with several embodiments of the present disclosure. Method 100 includes receiving a query at operation 102. Operation 102 may include, for example, receiving a request for data on a topic, such as a patient's adherence to a medication plan. The information may be received from an external source, such as a client server.

Method 100 further includes acquiring data at operation 104. Operation 104 may include, for example, sending a request to a device and receiving data in response. One example of operation 104 is receiving a dataset from an application executing on a user's mobile device (such as a medication tracker application). In some embodiments, the data in the dataset may be tagged to identify data fields represented in the dataset. For example, the dataset may indicate that it includes information identifying a patient, a medication administered, time(s) of the administration, etc. In some embodiments, operation 104 may include identifying data fields in the dataset (e.g., if the dataset is not explicitly tagged). In some embodiments, the data may be received from the same source as the query (for example, a client may submit a query to a system performing method 100 regarding the client's own data).

Method 100 further includes determining an expected data shape at operation 106. A "data shape," as used herein, refers to properties of the data such as data type (e.g., a format or filetype of the data), a list of data fields included in the data (e.g., user ID, medication ID, administration events, etc.), a size of the dataset (e.g., a number of rows/columns, a file size, etc.), and/or values of some of the data (e.g., that the medication ID is "Acetaminophen" or a numeric code corresponding to Acetaminophen). Operation 106 may include, for example, predicting an expected shape of a dataset that would be an adequate response to the query. For example, a query regarding patient John Doe's adherence to an Acetaminophen medication plan. An expected shape of data responsive to such a query may indicate that the data should include fields describing patient identity, medication identity, and number of medication administrations. The shape may further indicate that the value of the patient ID field should be (or reference) "John Doe" (as data about a different patient's medication administrations may be irrelevant at best and actively misleading at worst) and that the value of the medication ID field should be "Acetaminophen."

The expected shape of the data can be determined based on the received query, the received data, existing industry standards, and/or a combination, as described in further detail with reference to FIG. 2, below. In some embodiments, operation 106 may include receiving an expected data shape from an external source (which may be the source of the query, the source of the data, or a different source) or loading one from storage. An example expected data shape is depicted in FIG. 4.

Method 100 further includes determining a confidence factor at operation 108. Operation 108 may include, for example, comparing a shape of the received data to an expected data shape. In general, the confidence factor indicates whether the received dataset includes the data fields and values that the expected shape indicates it should. Put differently, it represents a degree of confidence in the responsiveness of the data (e.g., a degree to which data suffices as a complete answer to the query). For example, a high confidence factor indicates that the data is more likely to suffice as a response to the query, while a low confidence factor may indicate that the data is likely incomplete or that more data is needed.

The specific method by which the confidence factor is determined may vary depending upon embodiment and use case. In some embodiments, the confidence factor may be a simple ratio of data fields in the received data to data fields making up the expected data shape. In some embodiments, the confidence factor may further account for data included that is not necessary (for example, if portions of the data received are irrelevant, this may result in a confidence factor penalty).

Method 100 further include submitting a response to the query at operation 110. Operation 110 may include, for example, sending the data received at operation 104 to the source of the query received at operation 102 (or, in some use cases, to a different source identified by the query). In some embodiments, operation 110 may also include sending the confidence factor. This may be particularly advantageous to some query sources (e.g., customers) in that it can enable a query source to more properly utilize the data. For example, even if a customer has a relatively low confidence level requirement (included in the query), the customer may benefit from knowing that data contained in a particular reply has an exceptionally high confidence rating. In some embodiments, operation 110 may only send data whose shape matches the expected shape. For example, data sent in response to a medication adherence query may be expected to include data fields such as medication identification data, patient identification data, and medication administration data. If the received data includes the expected data fields but also includes irrelevant data fields such as, for example, patient physician visit dates, operation 110 may include removing the irrelevant data before submitting the relevant data in response to the query.

Figure 2:
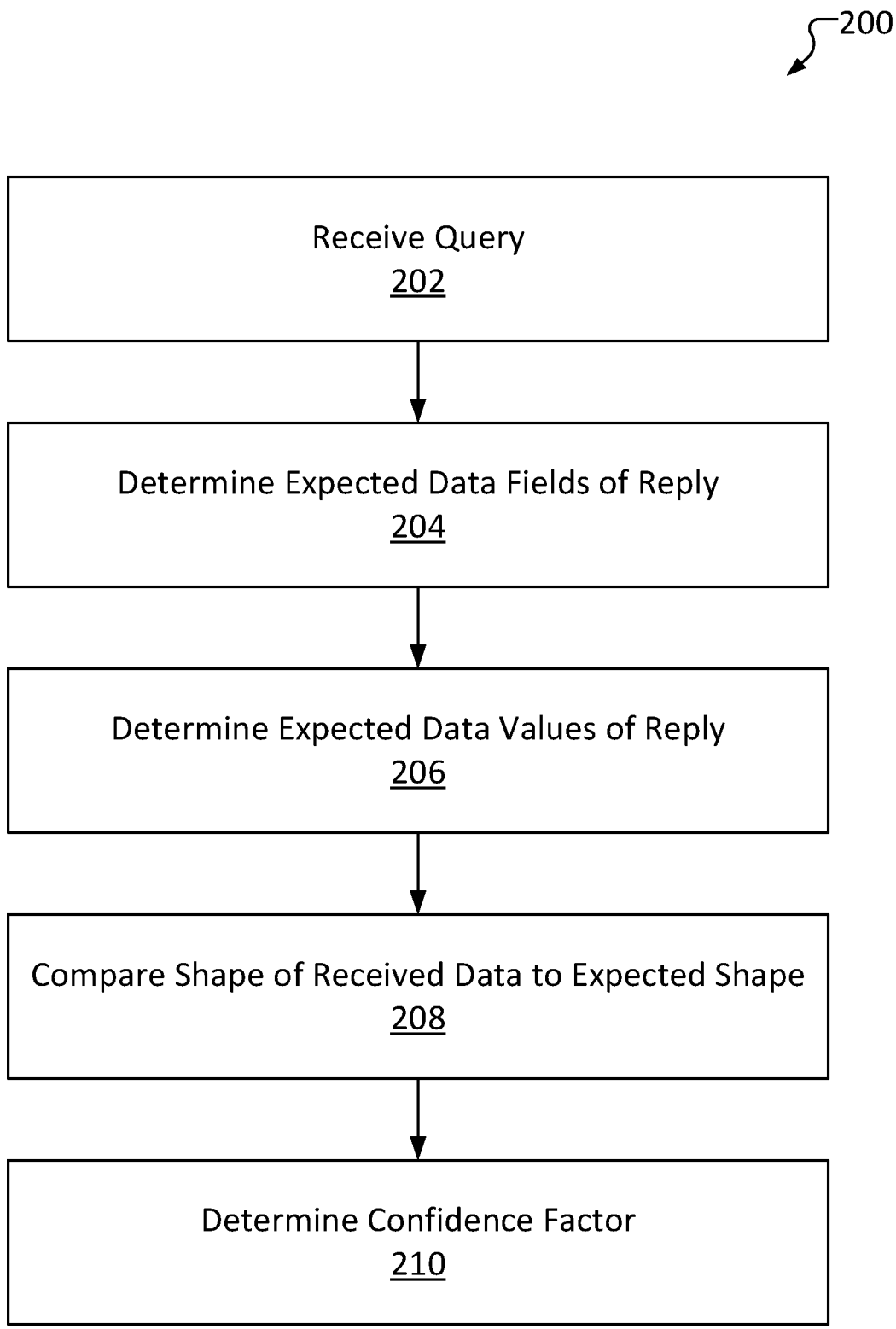
FIG. 2 is a detailed data shape model generation and comparison method, consistent with several embodiments of the present disclosure.

FIG. 2 is a more detailed method 200 of determining and comparing expected and received data shapes, consistent with several embodiments of the present disclosure. Method 200 includes receiving a query at operation 202. Operation 202 may include, for example, receiving a request for data on a topic, such as a patient's adherence to a medication plan. The information may be received from an external source, such as a client server.

Method 200 further includes determining expected data fields of a reply to the query at operation 204. Operation 204 may include, for example, analyzing the query and selecting one or more data fields from a predetermined, generalized list. The data fields may be selected such that a dataset containing each of the selected data fields may form a cohesive reply to the query. As an example, a reply to a "medication adherence" query may require a "patient identifier" field (to allow the client to verify that the data pertains to the correct patient), a medication ID field (to enable the client to verify that the patient was administered the correct medication), and a dose field (to enable the client to verify that the medication was administered with the appropriate dose).

In some embodiments, data fields may be selected based on preprogrammed behavior. For example, operation 204 may include analyzing the query and determining which fields will need to be included in a reply based on the query. In some embodiments, data fields may be based on historical data. For example, operation 204 may include comparing the query to past queries, selecting fields based on the replies to the most similar previous queries. In some embodiments, data fields may be selected via manual user review. For example, operation 204 may include a user of a system performing method 200 reviewing the query and entering (via one or more user input devices) a list of data fields that a reply to the query should include. Combinations of the above are also considered (e.g., operation 204 may include both manual user review and automated analysis of the query).

In some embodiments, a system may receive a query, identify a general industry of the query (e.g., healthcare), select a preexisting generalized shape based on the industry, and then refine the generalized shape into an expected shape.

Method 200 further includes determining expected data values of a reply to the query at operation 206. Operation 206 may include, for example, analyzing the query and determining if a value of any of the data fields determined at operation 204 can be predicted (and predicting the value if so). For example, if a query pertains to John Doe's medication plan adherence, and operation 204 identifies at least a "patient ID" field, operation 206 may include determining that a value of the "patient ID" field should include (or decode to, etc.) "John Doe." Similarly, if the query indicates that the medication plan is for administration of Acetaminophen, operation 206 may include determining that a value of the "medication ID" field should include "Acetaminophen." However, not all data fields will have expected values; for example, a "dose timestamp" data field may not have a specific expected value (unless the query indicates that the dose should be administered within a certain time window), but the field itself may be still expected to be included regardless of its value. In some use cases, no data fields will have expected values.

The expected fields and values determined in operations 204 and 206, respectively may form an "expected shape" of a reply to the query. Method 200 further includes comparing a shape of received data to an expected shape of data at operation 208. Operation 208 may include, for example, determining whether the received dataset is missing any expected data fields, or if the values of any expected data fields are "wrong" (different from expected values).

Operation 208 may further include determining whether any included data fields are "irrelevant" (for example, a patient's height may not be relevant to their adherence to a medication plan). Inclusion of irrelevant data may result in unnecessary privacy risks, resource (e.g., bandwidth) consumption, or even potentially obscuring the requested data; information about a first patient, if submitted in a reply to a query about a second patient (even alongside the appropriate data about the second patient), may be erroneously interpreted by the client as relevant to the second patient.

Method 200 further includes determining a confidence factor at operation 210. Operation 210 may include, for example, compiling the information resulting from the comparison of operation 208 into a number (such as a value from 0 to 1). The confidence factor may represent a confidence that the received data forms a complete reply to the query. In other words, a high confidence factor may indicate that the received data includes most, if not all, of the expected data fields, and that the values of those data fields are their expected values.

In determining the confidence factor, different expected fields and values may have different "weights." For example, an expected patient value (e.g., a patient name such as "John Doe") may have a significant weight, such that an incorrect patient ID results in a heavy penalty to the confidence factor (as the received data would likely constitute a poor reply to the query because it pertains to an entirely different patient). However, in the case of a medication adherence plan query, a dosage timing being off from an expected value may have a relatively small weight, as confidence in the data's validity as a reply to the query is unaffected. In other words, the patient failing to adhere to the plan does not impact the confidence rating; the confidence rating describes how accurately the data answers the query. It does not describe the answer to the query itself.

The confidence factor can be utilized to make various decisions regarding what to do with the received data (e.g., whether to seek out additional data or to transmit a reply), as described below in further detail with reference to FIG. 3. Depending upon embodiment/query, the confidence factor may be included in a reply to the query.

Figure 3:
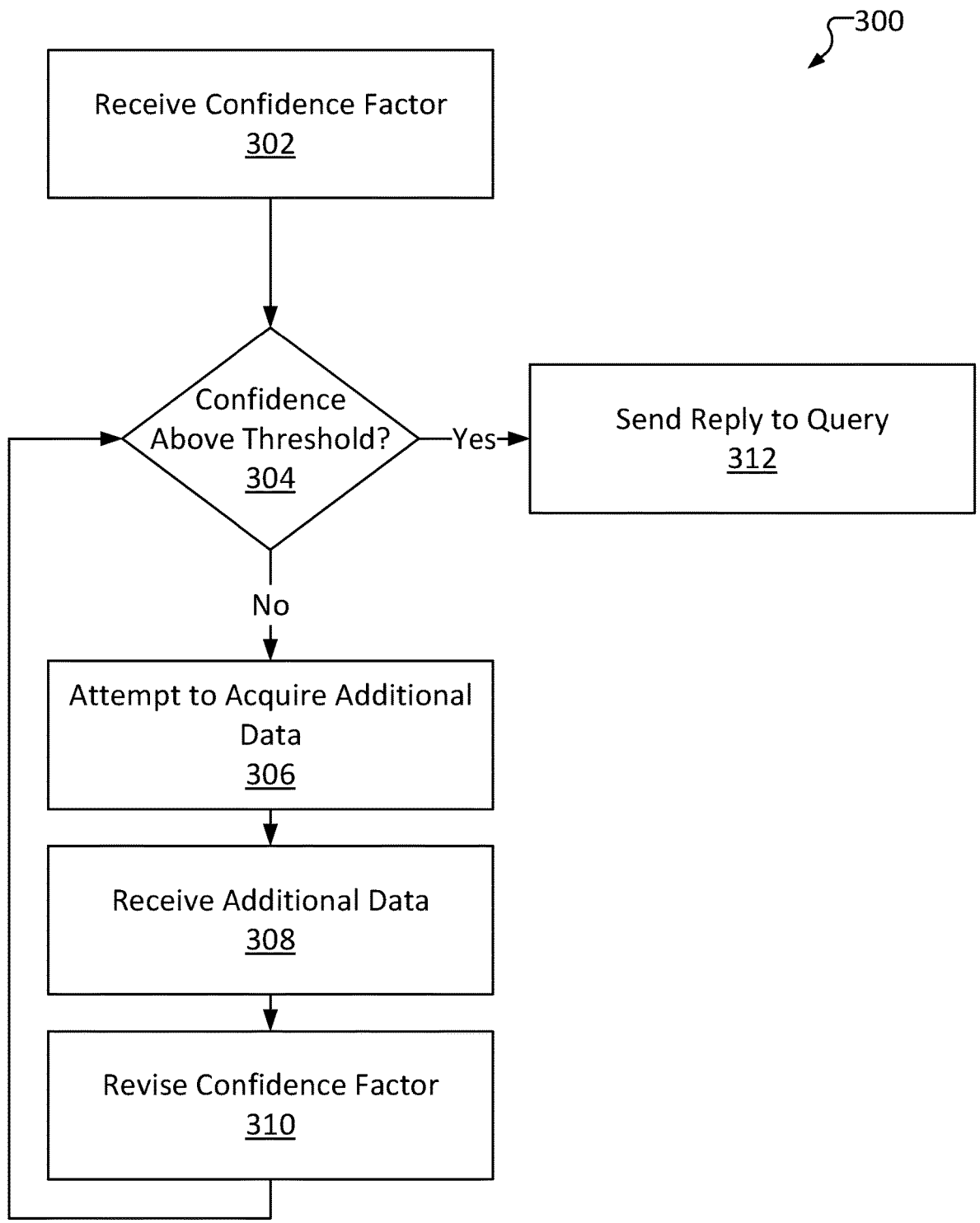
FIG. 3 is a high-level data-shape-based confidence evaluation method, consistent with several embodiments of the present disclosure.

FIG. 3 is a high-level data-shape-based confidence evaluation method 300, consistent with several embodiments of the present disclosure. Method 300 includes receiving a confidence factor at operation 302. Operation 302 may include, for example, determining a confidence factor describing a confidence that a received dataset will answer a received query (such as via method 200 of FIG. 2).

Method 300 further includes determining whether the confidence factor is above a threshold at operation 304. Operation 304 may include, for example, comparing the confidence factor to a preset threshold (e.g., 0.8, 0.9). The threshold may be determined based on the query, the query may explicitly specify the threshold, or a default threshold may be utilized. In some embodiments, a query (or setting) may imply that no threshold comparison is necessary, in which case operation 304 may be skipped (for example, a client may wish to gather all query replies, so long as it is aware of which responses may be insufficient; this may further enable the client to make its own determinations as to which data to trust). In general, operation 304 determines whether the received dataset will form a sufficient reply to the query.

If the confidence factor is above the threshold (304 "Yes"), or if 304 is skipped, method 300 further includes sending a reply to the query at operation 312. Operation 312 may include, for example, forwarding the raw (unmodified) dataset to a client or other external entity. In some embodiments, operation 312 may include modifying the received data to fit a specific format and/or filetype. In some embodiments, the confidence factor may be included in the reply.

If the confidence factor is not above the threshold (304 "No"), method 300 further includes attempting to acquire additional data at operation 306. Operation 306 may include, for example, waiting for a user device to sync, transmitting a request for additional data to an external entity (such as a physician's office or a database), etc.

In some embodiments, operation 306 may include selecting a supplemental data acquisition approach based on the data or query. For example, the received query may indicate a "backup" data source for a system performing method 300 to utilize (such as a patient's provider's server). Operation 306 may also depend upon the missing data. For example, if a missing data field is likely to be received via a periodic device sync (such as a medication administration event field), then operation 306 may be more likely to include waiting for a device sync. As a further example, if the missing data field is not likely to be received via a periodic device sync, operation 306 may transmit a request to a secondary source rather than wait for a sync. In some embodiments, operation 306 may include sending a request or reminder to a user device (e.g., to prompt a user of the user device to either sync the device or perform another action, such as administering medication).

Method 300 further includes receiving additional data at operation 308. Operation 308 may include, for example, receiving a supplemental dataset via a device sync or in response to a request made as part of operation 306. The additional data may be checked to determine whether it includes previously missing data fields and/or values (such as those identified via operation 208). In some embodiments, the additional data may be combined with the previously-obtained data into a new dataset, which is then checked for completeness (e.g., a shape of the new dataset may be compared to the expected shape of a reply).

Method 300 further includes revising the confidence factor at operation 310. Operation 310 may be performed in a manner substantially similar to operation 210 of method 200, as described with reference to FIG. 2. Operation 310 may include, for example, compiling a number (such as a value from 0 to 1) representing a confidence that the received data and additional data form a complete reply to the query. In other words, a high confidence factor may indicate that the data includes most, if not all, of the expected data fields, and that the values of those data fields are their expected values.

With a revised confidence factor, method 300 may loop to operation 304, comparing the revised confidence factor to the threshold. Operations 304-310 may be repeated until the confidence factor meets the threshold (at which point a reply will be sent via operation 312). In some embodiments, a cap on the number of loops may be implemented, set by a user of a system performing method 300 or outlined in the query.

FIG. 4 is a block diagram illustrating an example expected data shape 401 consistent with several embodiments of the present disclosure. FIG. 4 depicts a "generalized" data shape 400 including a plurality of different data fields. Generalized shape 400 may be an industry standard, or may be developed over time based on past queries and/or replies to those queries.

Expected shape 401 includes data fields and/or values determined to be particularly relevant to a query. Note that, in some instances, expected shape 401 may be identical to generalized shape 400. However, expected shape 401 may also include data fields/values not found in generalized shape 400. Similarly, expected shape 401 may not include any data fields or values of generalized shape 400. Overall, expected shape 401 may commonly be a subset of generalized shape 400.

In the example depicted in FIG. 4, generalized shape 400 is a "healthcare"-related shape (including common healthcare data fields such as patient ID 402, weight field 418, etc.). The example expected shape 401 depicted in FIG. 4 includes data fields and/or values determined to be relevant to a reply to a query regarding patient medication plan adherence.

Expected shape 401 includes patient field 402. A value of patient field 402 may include a patient ID such as a name (e.g., "John Doe"), a patient number, etc. Expected shape 401 also includes medication field 404. Values of medication field 404 may include one or more medication IDs. For example, a value of medication 1 405 may be "Acetaminophen," a value of medication 2 406 may be "Ibuprofen," etc.

Expected shape 401 further includes medication administration field 408. Medication administration field 408 may include values identifying when medication is administered to the patient identified in patient field 402. Medication administration field 408 includes its own data fields for each administration (dose 1 409 and dose 2 410). Dose 1 409 and dose 2 410 may include specific data including how much medication was administered/estimated to be absorbed or bioavailable.

Generalized shape 400 includes all of the fields of expected shape 401. Generalized shape 400 further includes provider field 412, whose value may identify a provider associated with the patient identified in patient field 402 (e.g., a physician). Generalized shape 400 further includes prescription field 414, which may include values identifying a prescription associated with the patient. Prescription field 414 is not necessarily relevant to an adherence query, as the medication in question may be an "over-the-counter" medication, or the query may state its own parameters outside of a prescription.

Generalized shape 400 also includes blood pressure field 416 (whose value may identify a patient's blood pressure), weight field 418 (whose value may identify a patient's weight), and height field 420 (whose value may identify a patient's height). As will be appreciated by one of skill in the art, these may not be relevant to a medication adherence query (outside of rare special cases), in which case they may be omitted from expected shape 401.

Figure 5:
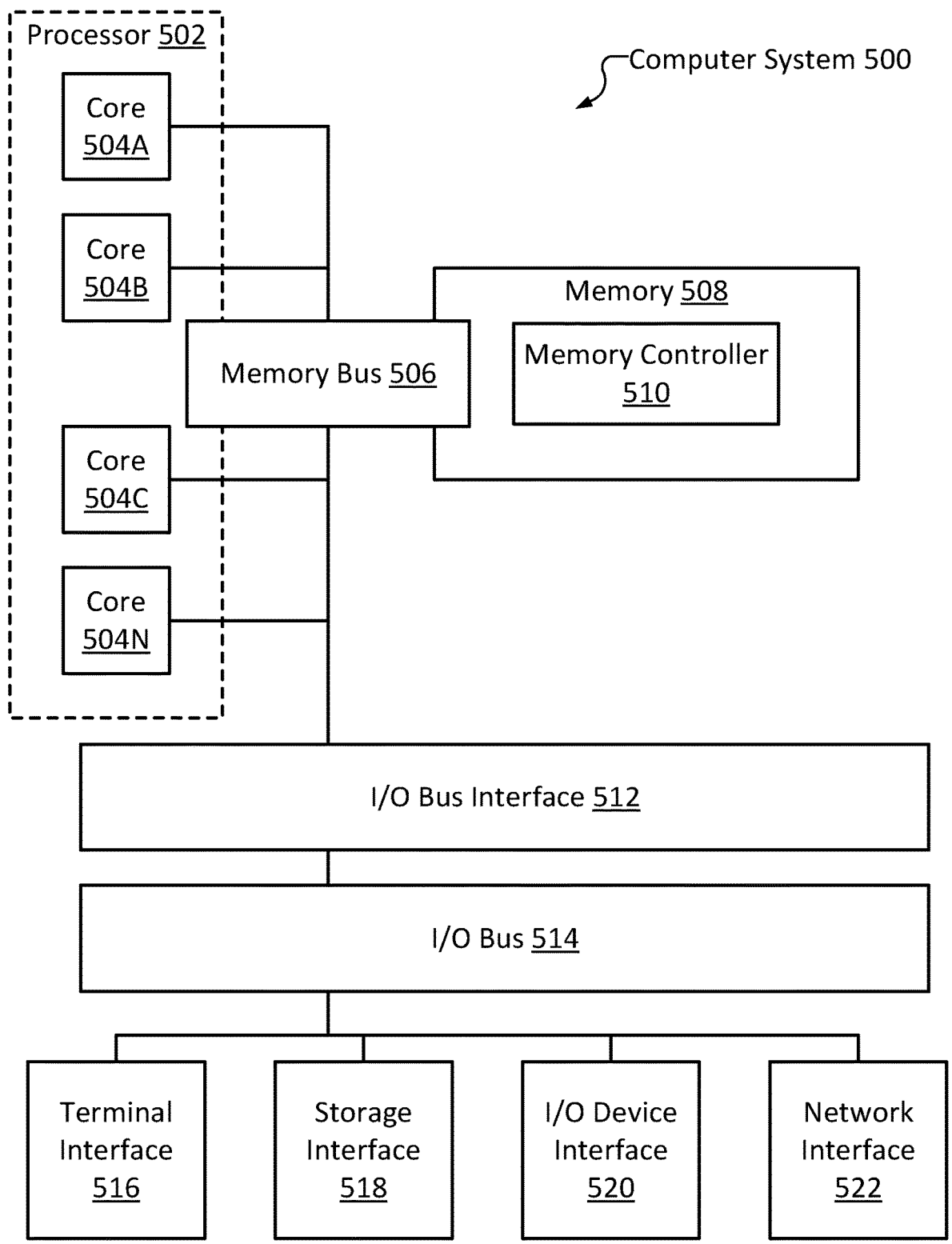
FIG. 5 illustrates a high-level block diagram of an example computer system that may be used in implementing embodiments of the present disclosure.

Referring now to FIG. 5, shown is a high-level block diagram of an example computer system 500 that may be configured to perform various aspects of the present disclosure, including, for example, methods 100, 200 and 300. The example computer system 500 may be used in implementing one or more of the methods or modules, and any related functions or operations, described herein (e.g., using one or more processor circuits or computer processors of the computer), in accordance with embodiments of the present disclosure. In some embodiments, the major components of the computer system 500 may comprise one or more CPUs 502, a memory subsystem 508, a terminal interface 516, a storage interface 518, an I/O (Input/Output) device interface 520, and a network interface 522, all of which may be communicatively coupled, directly or indirectly, for inter-component communication via a memory bus 506, an I/O bus 514, and an I/O bus interface unit 512.

The computer system 500 may contain one or more general-purpose programmable central processing units (CPUs) 502, some or all of which may include one or more cores 504A, 504B, 504C, and 504D, herein generically referred to as the CPU 502. In some embodiments, the computer system 500 may contain multiple processors typical of a relatively large system; however, in other embodiments the computer system 500 may alternatively be a single CPU system. Each CPU 502 may execute instructions stored in the memory subsystem 508 on a CPU core 504 and may comprise one or more levels of on-board cache.

In some embodiments, the memory subsystem 508 may comprise a random-access semiconductor memory, storage device, or storage medium (either volatile or non-volatile) for storing data and programs. In some embodiments, the memory subsystem 508 may represent the entire virtual memory of the computer system 500 and may also include the virtual memory of other computer systems coupled to the computer system 500 or connected via a network. The memory subsystem 508 may be conceptually a single monolithic entity, but, in some embodiments, the memory subsystem 508 may be a more complex arrangement, such as a hierarchy of caches and other memory devices. For example, memory may exist in multiple levels of caches, and these caches may be further divided by function, so that one cache holds instructions while another holds non-instruction data, which is used by the processor or processors. Memory may be further distributed and associated with different CPUs or sets of CPUs, as is known in any of various so-called non-uniform memory access (NUMA) computer architectures. In some embodiments, the main memory or memory subsystem 804 may contain elements for control and flow of memory used by the CPU 502. This may include a memory controller 510.

Although the memory bus 506 is shown in FIG. 5 as a single bus structure providing a direct communication path among the CPU 502, the memory subsystem 508, and the I/O bus interface 512, the memory bus 506 may, in some embodiments, comprise multiple different buses or communication paths, which may be arranged in any of various forms, such as point-to-point links in hierarchical, star or web configurations, multiple hierarchical buses, parallel and redundant paths, or any other appropriate type of configuration. Furthermore, while the I/O bus interface 512 and the I/O bus 514 are shown as single respective units, the computer system 500 may, in some embodiments, contain multiple I/O bus interface units 512, multiple I/O buses 514, or both. Further, while multiple I/O interface units are shown, which separate the I/O bus 514 from various communications paths running to the various I/O devices, in other embodiments some or all of the I/O devices may be connected directly to one or more system I/O buses.

In some embodiments, the computer system 500 may be a multi-user mainframe computer system, a single-user system, or a server computer or similar device that has little or no direct user interface but receives requests from other computer systems (clients). Further, in some embodiments, the computer system 500 may be implemented as a desktop computer, portable computer, laptop or notebook computer, tablet computer, pocket computer, telephone, smart phone, mobile device, or any other appropriate type of electronic device.

It is noted that FIG. 5 is intended to depict the representative major components of an exemplary computer system 500. In some embodiments, however, individual components may have greater or lesser complexity than as represented in FIG. 5, components other than or in addition to those shown in FIG. 5 may be present, and the number, type, and configuration of such components may vary.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be accomplished as one step, executed concurrently, substantially concurrently, in a partially or wholly temporally overlapping manner, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The descriptions of the various embodiments of the present disclosure have been presented for purposes of illustration but are not intended to be exhaustive or limited to the embodiments disclosed. Many modifications and variations will be apparent to those of ordinary skill in the art without departing from the scope and spirit of the described embodiments. The terminology used herein was chosen to explain the principles of the embodiments, the practical application or technical improvement over technologies found in the marketplace, or to enable others of ordinary skill in the art to understand the embodiments disclosed herein.

What is claimed is:

1. A method, comprising:
   receiving a query from a query source;
   receiving a dataset;
   comparing the query to historical queries;
   acquiring, based on the comparing the query, an expected data shape, wherein the expected data shape is developed over time based on historical queries and historical replies;
   determining a data shape of the dataset;
   comparing the data shape to the expected data shape;
   determining, based on the comparing the data shape, a confidence factor;
   detecting that the confidence factor is above a confidence threshold;
   selecting, based on the detecting, the dataset; and
   transmitting, in response to the detecting, a reply to the query source in response to the query, the reply based on the dataset.

2. The method of claim 1, wherein the acquiring includes determining, based on the query, one or more expected data fields of the data, wherein the expected data shape is based on the expected data fields.

3. The method of claim 1, wherein the acquiring includes:
   identifying, based on the query, an industry; and
   selecting a generalized data shape based on the industry, wherein the expected data shape is based on the generalized data shape.

4. The method of claim 3, wherein the expected data shape consists of the generalized data shape.

5. The method of claim 1, further comprising:
   receiving a second query from a second query source;
   receiving an additional dataset;
   determining a second data shape based on the additional dataset;
   acquiring a second expected data shape;
   comparing the second data shape to the second expected data shape;
   determining, based on the comparing the second data shape, a second confidence factor;
   detecting that the second confidence factor is below a second confidence threshold; and
   acquiring further data.

6. The method of claim 1, further comprising removing, after the selecting, data from the dataset that is irrelevant to the query, wherein the transmitting comprises transmitting the dataset after the removal.

7. A system comprising:
   a memory; and
   a central processing unit (CPU) coupled to the memory, the CPU configured to:
   receive a query from a query source;
   receive a dataset;
   compare the query to historical queries;
   acquire, based on the comparing the query, an expected data shape, wherein the expected data shape is developed over time based on historical queries and historical replies;
   determine a data shape of the dataset;
   compare the data shape to the expected data shape;
   conclude, based on the comparing the data shape, that the dataset is responsive to the query;
   selecting, based on the concluding, the dataset;
   transmit, based on the concluding, a reply to the query source in response to the query, the reply based on the dataset.

8. The system of claim 7, wherein the acquiring includes determining, based on the query, one or more expected data fields of the data, wherein the expected data shape is based on the expected data fields.

9. The system of claim 7, wherein the acquiring includes:
   identifying, based on the query, an industry; and selecting a generalized data shape based on the industry, wherein the expected data shape is based on the generalized data shape.

10. The system of claim 9, wherein the expected data shape consists of the generalized data shape.

11. The system of claim 7, wherein the CPU is further configured to:
receive a second query from a second query source;
receive an additional dataset;
determine a second data shape based on the additional dataset;
acquire a second expected data shape;
compare the second data shape to the second expected data shape;
determine, based on the comparing the second data shape, a confidence factor;
detect that the confidence factor is below a confidence threshold; and
acquire further data.

12. The system of claim 11, wherein the CPU is further configured to:
determine, based on the additional dataset and the further data, a second confidence factor;
detect that the second confidence factor is above the confidence threshold; and
transmit, in response to the detecting that the second confidence factor is above the confidence threshold, a second reply to the second query source in response to the second query, the second reply based on the additional dataset and the further data.

13. The system of claim 7, wherein the CPU is further configured to:
receive a second query from a second query source;
receive an additional dataset;
determine a second data shape based on the additional dataset;
acquire a second expected data shape;
compare the second data shape to the second expected data shape;
determine, based on the comparing the second data shape, a confidence factor;
detect that the confidence factor is above a confidence threshold; and
transmit, in response to the detecting, a second reply to the second query source in response to the second query, the second reply based on the additional dataset.

14. A computer program product, the computer program product comprising a computer readable storage medium having program instructions embodied therewith, the program instructions executable by a computer to cause the computer to:
receive a query from a query source;
receive a dataset;
compare the query to historical queries;
acquire, based on the comparing the query, an expected data shape, wherein the expected data shape is developed over time based on historical queries and historical replies and is based on an expected data field;
determine a data shape of the dataset, wherein the data shape is based on a data field of the dataset;
compare the data shape to the expected data shape, wherein the comparing comprises determining whether the data field matches the expected data field;
determine, based on the comparing the data shape, a confidence factor;
detect that the confidence factor is above a confidence threshold;
select, based on the detecting, the dataset; and
transmit a reply to the query source in response to the query, the reply based on the dataset and the confidence factor.

15. The computer program product of claim 14, wherein the acquiring includes determining, based on the query, the expected data field.

16. The computer program product of claim 14, wherein the acquiring includes:
identifying, based on the query, an industry; and
selecting a generalized data shape based on the industry, wherein the expected data shape is based on the generalized data shape.

17. The computer program product of claim 16, wherein the expected data shape consists of the generalized data shape.

18. The computer program product of claim 14, wherein the instructions further cause the computer to:
receive a second query from a second query source;
receive an additional dataset;
determine a second data shape based on the additional dataset;
acquire a second expected data shape;
compare the second data shape to the second expected data shape;
determine, based on the comparing the second data shape, a second confidence factor;
detect that the second confidence factor is below the confidence threshold; and
acquire further data.

19. The computer program product of claim 18, wherein the instructions further cause the computer to:
determine, based on the additional dataset and the further data, a third confidence factor;
detect that the third confidence factor is above the confidence threshold; and
transmit, in response to the detecting that the third confidence factor is above the confidence threshold, a second reply to the second query source in response to the second query, the second reply based on the additional dataset and the further data.

20. The computer program product of claim 14, wherein the instructions further cause the computer to:
receive a second query from a second query source;
receive an additional dataset;
determine a second data shape based on the additional dataset;
acquire a second expected data shape;
compare the second data shape to the second expected data shape;
determine, based on the comparing the second data shape, a second confidence factor;
detect that the second confidence factor is above the confidence threshold; and
transmit, in response to the detecting, a second reply to the second query source in response to the second query, the second reply based on the additional dataset.

* * * * *